United States Patent
Kölbel et al.

(10) Patent No.: US 11,992,219 B2
(45) Date of Patent: May 28, 2024

(54) IMPLANTABLE MEDICAL DEVICE AND ASSEMBLY

(71) Applicant: Cook Medical Technologies LLC, Bloomington, IN (US)

(72) Inventors: Tilo Kölbel, Hamburg (DE); John Mogensen, Hvidovre (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 17/830,768

(22) Filed: Jun. 2, 2022

(65) Prior Publication Data
US 2022/0395278 A1 Dec. 15, 2022

(30) Foreign Application Priority Data

Jun. 10, 2021 (GB) .................................... 2108304

(51) Int. Cl.
*A61B 17/12* (2006.01)
*A61F 2/07* (2013.01)
*A61F 2/966* (2013.01)

(52) U.S. Cl.
CPC .. *A61B 17/12118* (2013.01); *A61B 17/12031* (2013.01); *A61B 17/12159* (2013.01);
(Continued)

(58) Field of Classification Search
CPC ........ A61B 17/12118; A61B 17/12031; A61B 2017/00336; A61B 2017/1205;
(Continued)

(56) References Cited

U.S. PATENT DOCUMENTS

| | | |
|---|---|---|
| 4,922,905 A | 5/1990 | Strecker |
| 5,382,261 A | 1/1995 | Palmaz |

(Continued)

FOREIGN PATENT DOCUMENTS

| | | |
|---|---|---|
| CN | 203852449 | 10/2014 |
| EP | 2676638 | 12/2013 |

(Continued)

OTHER PUBLICATIONS

Search and Examination Report for Great Britain Application No. 21083043, dated Oct. 13, 2021, 7 gages
(Continued)

*Primary Examiner* — Julian W Woo
*Assistant Examiner* — Osama Nemer
(74) *Attorney, Agent, or Firm* — Crowell & Moring LLP

(57) ABSTRACT

Disclosed is a false lumen closure assembly for closing a false lumen in a body vessel including a compressed false lumen occluder, a carrier catheter and a retractable sheath. The compressed false lumen occluder includes a stent graft including at least one occlusive barrier across the stent graft to occlude blood flow through an interior of the stent graft. The carrier catheter carries the false lumen occluder and extends from a proximal end proximal of the false lumen occluder to a distal end distal of the false lumen occluder, and passes the false lumen occluder exteriorly of the stent graft. The compressed false lumen occluder and at least part of the carrier catheter are disposed in a lumen of the retractable sheath.

20 Claims, 7 Drawing Sheets

(52) U.S. Cl.
CPC ............... *A61F 2/07* (2013.01); *A61F 2/966* (2013.01); *A61F 2250/001* (2013.01); *A61F 2250/0039* (2013.01)

(58) Field of Classification Search
CPC ......... A61B 17/12099; A61B 17/12109; A61F 2/07; A61F 2/966; A61F 2250/0039; A61F 2/962
See application file for complete search history.

(56) References Cited

U.S. PATENT DOCUMENTS

| | | | |
|---|---|---|---|
| 6,102,938 | A | 8/2000 | Evans et al. |
| 6,305,436 | B1 | 10/2001 | Andersen et al. |
| 6,926,689 | B2 | 8/2005 | Scheule |
| 7,278,430 | B2 | 10/2007 | Kumar |
| 7,314,480 | B2 * | 1/2008 | Eidenschink .......... A61F 2/958 604/103.05 |
| 8,012,192 | B2 * | 9/2011 | Eidenschink .......... A61F 2/958 606/198 |
| 8,038,710 | B2 | 10/2011 | Fearnot et al. |
| 8,226,707 | B2 * | 7/2012 | White .................. A61F 2/2427 623/1.12 |
| 8,480,726 | B2 | 7/2013 | Cunningham et al. |
| 8,540,760 | B2 | 9/2013 | Paul, Jr. et al. |
| 8,906,086 | B2 | 12/2014 | Roeder et al. |
| 8,986,338 | B2 | 3/2015 | Obermiller et al. |
| 9,149,382 | B2 * | 10/2015 | Greenberg ................ A61F 2/86 |
| 9,295,571 | B2 | 3/2016 | Newell et al. |
| 9,364,354 | B2 | 6/2016 | Ben-Muvhar et al. |
| 9,427,233 | B2 | 8/2016 | Fearnot et al. |
| 9,681,876 | B2 | 6/2017 | Cragg et al. |
| 11,229,539 | B2 | 1/2022 | Cully et al. |
| 2002/0198587 | A1 | 12/2002 | Greenberg et al. |
| 2004/0117004 | A1 | 6/2004 | Osborne et al. |
| 2005/0228434 | A1 | 10/2005 | Amplatz et al. |
| 2006/0173490 | A1 | 8/2006 | Lafontaine et al. |
| 2010/0106240 | A1 | 4/2010 | Duggal et al. |
| 2011/0054512 | A1 | 3/2011 | Hendriksen et al. |
| 2012/0116496 | A1 | 5/2012 | Chuter et al. |
| 2013/0079870 | A1 * | 3/2013 | Roeder ...................... A61F 2/07 623/1.35 |
| 2017/0056175 | A1 | 3/2017 | Chin et al. |
| 2019/0000483 | A1 * | 1/2019 | Mogensen ....... A61B 17/12036 |
| 2023/0031517 | A1 * | 2/2023 | Perkins ............ A61B 17/12031 |

FOREIGN PATENT DOCUMENTS

| | | | | |
|---|---|---|---|---|
| EP | 2609895 B1 | * | 11/2015 | ............... A61F 2/07 |
| EP | 3323360 A1 | | 5/2018 | |
| EP | 3421011 | | 1/2019 | |
| ES | 2694586 T3 | * | 12/2018 | ............. A61B 17/12 |
| GB | 2503000 A | | 12/2013 | |
| GB | 2525647 A | | 11/2015 | |
| GB | 2563880 A | * | 1/2019 | ....... A61B 17/12036 |
| JP | 5634523 B2 | * | 12/2014 | ............... A61F 2/07 |
| KR | 20200075758 A | * | 6/2020 | ....... A61B 17/12113 |
| WO | WO 97/27893 | | 8/1997 | |
| WO | WO 2008/022327 A2 | | 2/2008 | |
| WO | WO 2008/097590 | | 8/2008 | |
| WO | WO 2008/103572 A1 | | 8/2008 | |
| WO | WO 2016/064748 A1 | | 4/2016 | |
| WO | WO 2017/200866 A1 | | 11/2017 | |

OTHER PUBLICATIONS

Search and Examination Report for Great Britain Application No. 21083043, dated May 13, 2022, 5 pages.
Distal false lumen occlusion in aortic dissection with a homemade extra large vascular plug: the candy plug technique, J Endovasc Ther. Aug. 20, 2013(4):484-9.

* cited by examiner

IMPLANTABLE MEDICAL DEVICE AND ASSEMBLY

RELATED APPLICATIONS

The present patent document claims the benefit of priority to Great Britain Patent Application No. 2108304.3, filed Jun. 10, 2021, and entitled "Implantable Medical Device and Assembly," the entire contents of which is incorporated herein in its entirety.

BACKGROUND

1. Technical Field

The present application relates to implantable medical devices, assemblies and methods, in particular to a false lumen closure assembly, occluder, and method.

2. Background

A false lumen caused by an aortic dissection may be treated by closing the upstream end of the false lumen for example with a stent graft. However, in some instances, the false lumen can still receive backflow from downstream tears in the false lumen wall. One way to treat this is to use an occluding device, in particular a candy plug including a valve element. Examples of implantable medical devices with a valve member for preventing backflow through a false lumen of a dissection can be found in EP 3 421 011, also published as U.S. Pat. No. 11,229,539 ("Implantable Medical Device Including Valve Member").

SUMMARY

The present invention provides improved false lumen closure assemblies, occluders, and methods. In one example there is provided a false lumen closure assembly for closing a false lumen in a body vessel, including: a compressed false lumen occluder including a stent graft, the stent graft including at least one occlusive barrier across the stent graft to occlude blood flow through an interior of the stent graft; a carrier catheter carrying the false lumen occluder, the carrier catheter extending from a proximal end proximal of the false lumen occluder to a distal end distal of the false lumen occluder, and passing the false lumen occluder exteriorly of the stent graft; a retractable sheath; wherein the compressed false lumen occluder and at least part of the carrier catheter are disposed in a lumen of the retractable sheath.

In some examples, the stent graft has a length and is hollow along a majority of the length in an expanded condition, optionally along at least 95% of the length in an expanded condition. For example, the stent graft is hollow along an entirety of the length in an expanded condition save for the at least one occlusive barrier. The at least one occlusive barrier may be a gapless graft material barrier across an end of the stent graft, for example the proximal or distal end of the stent graft.

The assembly may include a pusher member at least partly within the retractable sheath and proximal of the compressed false lumen occluder, to limit proximal movement of the false lumen occluder during delivery.

The carrier catheter may have a diameter of at least 0.5 mm, preferably at least 1 mm and the false lumen occluder including the stent graft may be wrapped around the carrier catheter. The carrier catheter laterally passes the compressed false lumen occluder. The carrier catheter may have a nose cone dilator at its proximal end.

In an expanded condition, the proximal end of the stent graft may have a diameter less than a diameter of the distal end of the stent graft, to facilitate retrieval of the carrier catheter. The stent graft may include a taper between the proximal and distal ends thereof.

A false lumen occluder is provided for closing a false lumen in a body vessel, the occluder including a stent graft, the stent graft being configured in an expanded condition to have a length, to be hollow along a majority of the length, to include at least one occlusive gapless graft material barrier across the stent graft to occlude blood flow through an interior of the stent graft, and to have a diameter greater than 15 mm. For example, the diameter is greater than 20 mm, and optionally greater than 30 mm.

The stent graft may include a stent or stents along its length, for example a series of Z-stents may be provided along its length.

The present invention also provides a method of closing a false lumen in a body vessel, including the stents of delivering a false lumen occluder to a false lumen in a body vessel; deploying the false lumen occluder in the false lumen; wherein the false lumen occluder includes a stent graft including at least one occlusive barrier across the stent graft to occlude blood flow through an interior of the stent graft.

Deploying the false lumen occluder may include retracting a sheath from the false lumen occluder which may allow the false lumen occluder to expand in the false lumen. Deploying the false lumen occlude may include releasing at least one trigger wire which may allow the false lumen occluder to expand in the false lumen. Deploying the false lumen may include enabling the stent graft to expand to seal against the wall of the false lumen such that the at least one occlusive barrier extends across and occludes the false lumen.

BRIEF DESCRIPTION OF THE DRAWINGS

Embodiments of the invention are described below, by way of example only, with reference to the accompanying drawings, in which.

DETAILED DESCRIPTION OF THE PREFERRED EMBODIMENTS

Described below are preferred embodiments of a false lumen occluder and assembly constructed according to the teachings herein, as well as associated methods. It is to be understood that the drawings are not to scale and are intended merely to be illustrative of the features and elements of the device, assembly and their components.

Throughout this specification the term proximal with respect with both human or animal vasculature will be used to refer to the region closest to the heart and similarly that part of the implantable medical device which when in use is closest to the heart, while the term distal will be used for the regions of the human or animal vasculature further from the heart and similarly those parts of the implantable medical device which in use are further from the heart. With regard to a deployment or introducer assembly or retrieval device, the term distal is also used to denote the part of the assembly which remains closest to the clinician during the medical procedure, and typically outside the patient, and the term proximal is also used to denote the end of the assembly which is furthest from the clinician and which is first fed endoluminally into the patient's vasculature.

The false lumen occluders and their constituent components described herein have what could be termed a compressed condition and an expanded condition.

Figure 1:
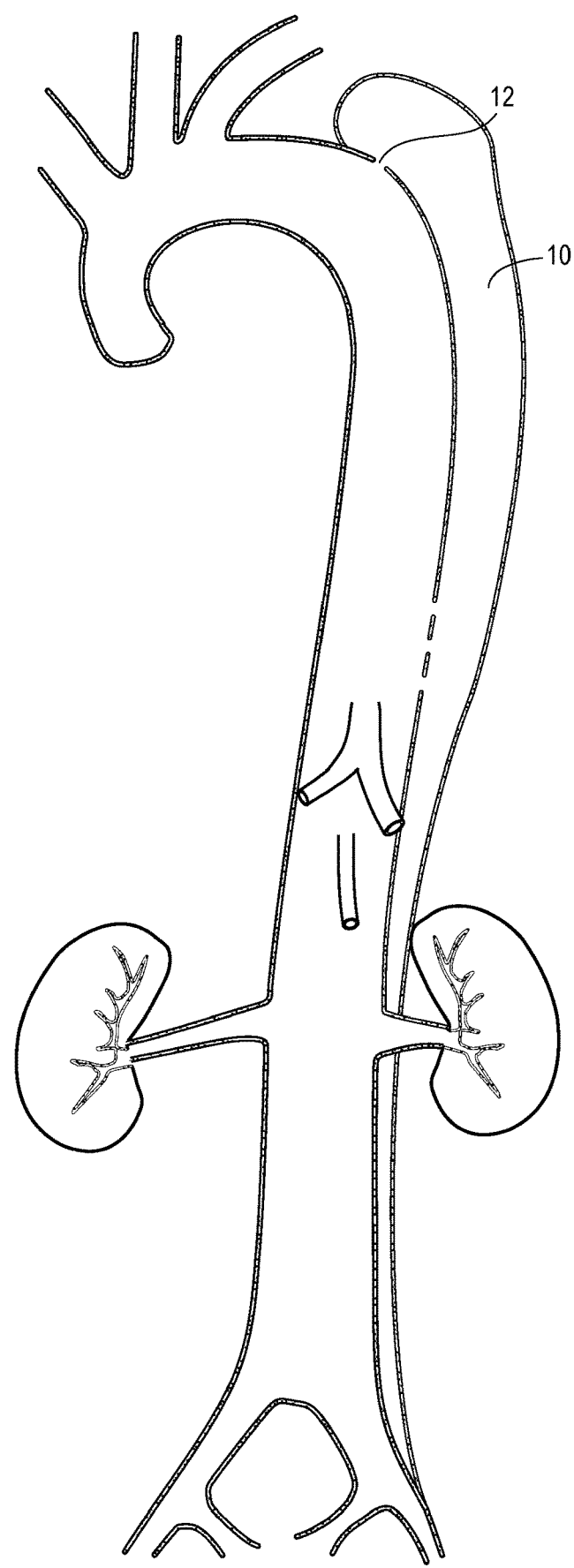
FIG. 1 is a schematic representation of a type B aortic dissection.
Figure 2:
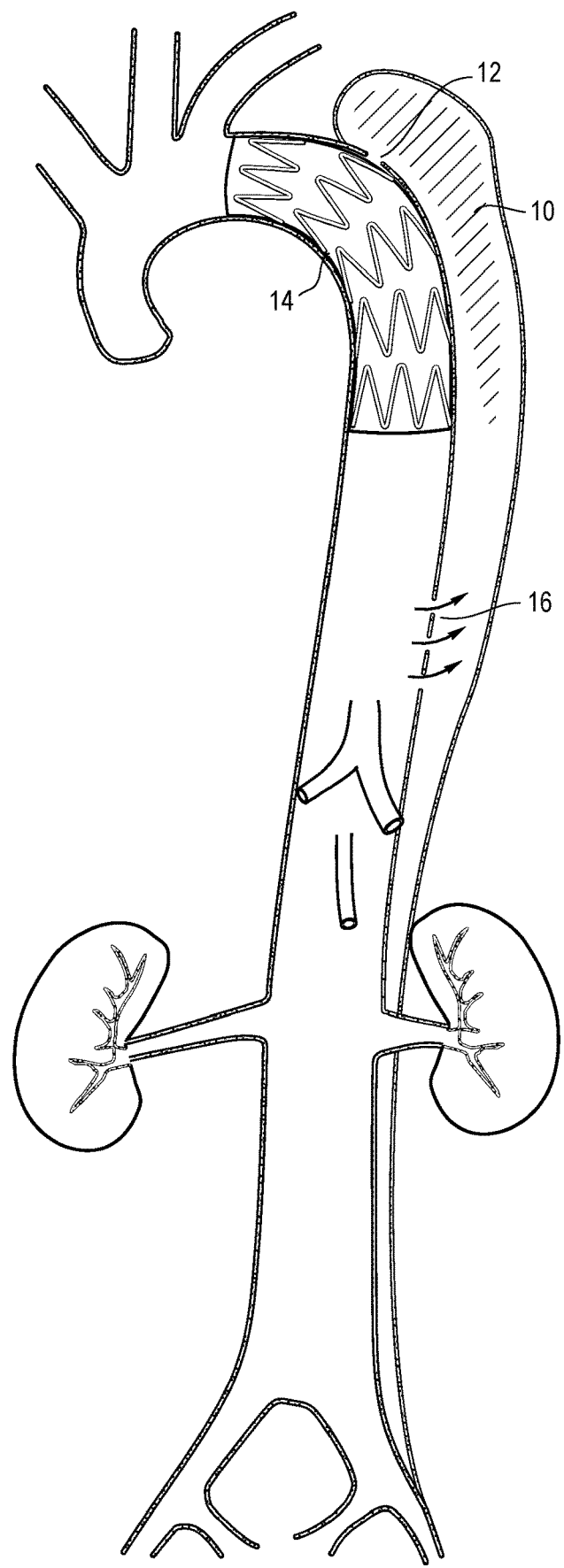
FIG. 2 is a schematic representation of the type B aortic dissection of FIG. 1 with a false lumen closed at its upstream end.

FIG. 1 shows a representation of a type B aortic dissection which has resulted in a false lumen 10. In FIG. 2, an upstream tear 12 in the aortic wall has been closed by a stent graft 14. However, the stent graft 14 does not extend all the way to the downstream end of the false lumen.

In this case, there are downstream tears 16 in the dissection membrane which allows backflow into the false lumen. This can prevent the false lumen from remodelling and lead to aneurysmal expansion of the false lumen in the thoracic aorta.

Figure 3:
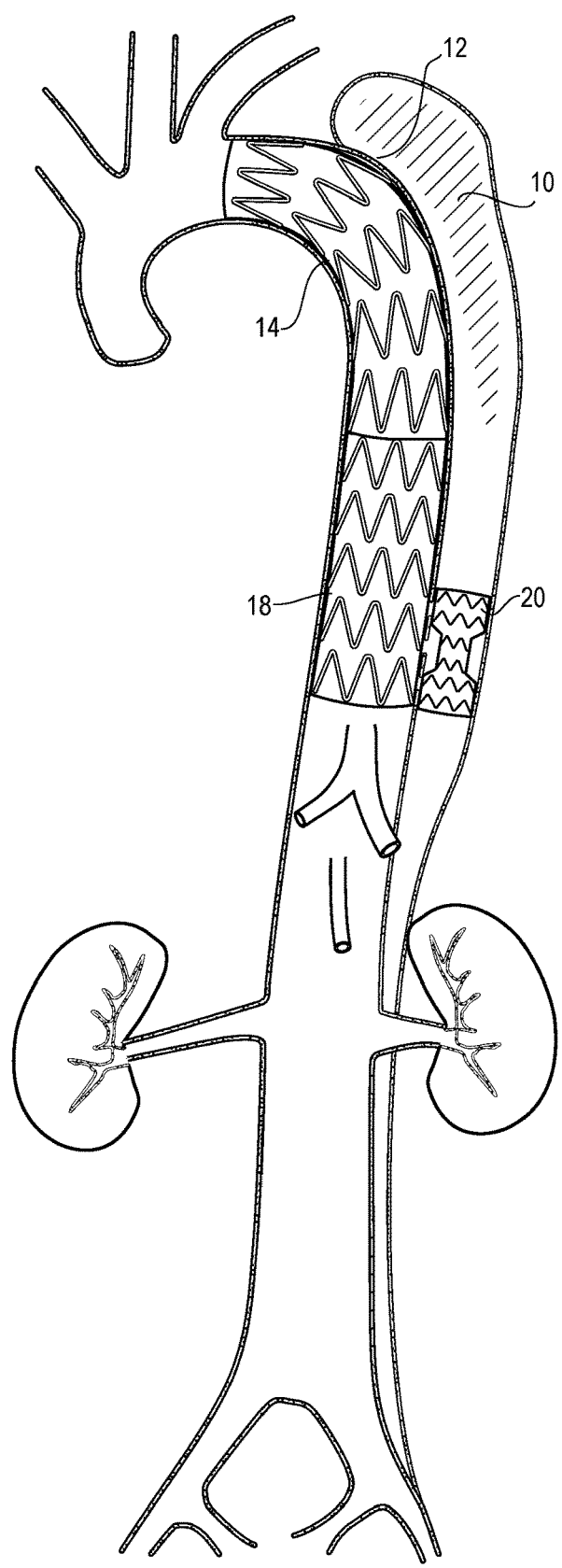
FIGS. 3 and 4 are schematic representations of a type B aortic dissection showing how back flow from downstream tears can be occluded using a known candy plug.
Figure 4:
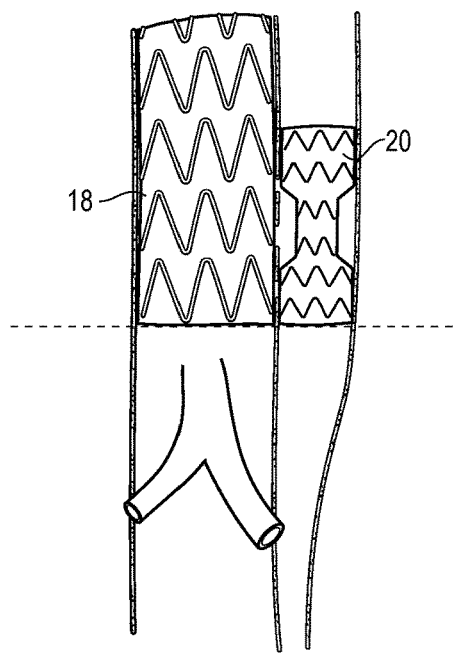

FIGS. 3 and 4 are representations of a known way of addressing the problem shown in FIGS. 1 and 2.

As can be seen in FIGS. 3 and 4, a further stent graft 18 has been deployed downstream of the first stent graft 14 in the aorta. In FIG. 4, a candy plug 20 has been deployed in the false lumen.

As can be seen in FIG. 4, the candy plug 20 has been deployed in the false lumen adjacent to or upstream of the tear 16. This can prevent the false lumen from receiving new blood from the tear 16.

Other devices for preventing backflow through a false lumen of dissection include implantable medical devices with valve members, such as disclosed in EP 3 421 011.

The various embodiments of the invention are able to provide false lumen occluders which can be compressed to a small delivery profile, and which can provide extremely rapid and effective occlusion. Embodiments are able to provide immediate closure of the false lumen to prevent back flow in a dissected artery or other vessel.

Figure 5:
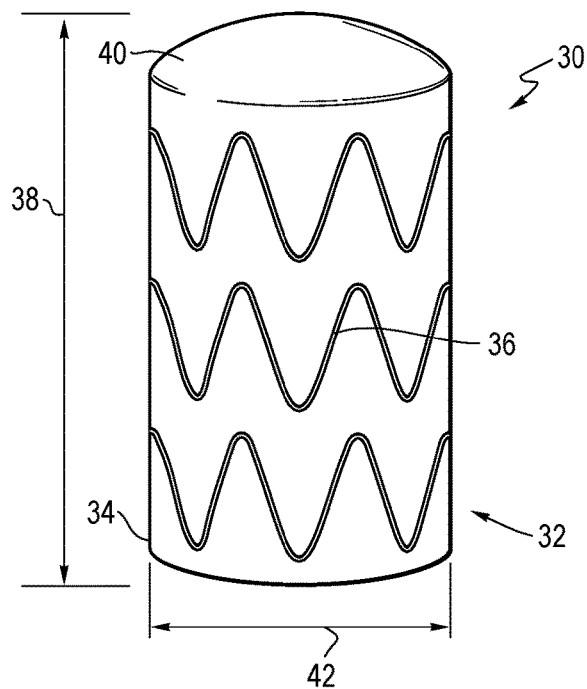
FIG. 5 is a false lumen occluder according to an embodiment of the invention.

FIG. 5 shows a false lumen occluder 30 in an expanded condition, which is in the form of a tubular stent graft closed at one end 40. The false lumen occluder 30 can be manufactured using well-known stent graft components. The occluder 30 includes and is in the form of a stent graft 32, including a tubular body 34 of graft material, supported by one or more stents 36. Here, the occluder 30 consists of the stent graft 32. As shown, the stent graft includes three stents 36 attached to the tubular body 34 and arranged along the length of the tubular body 34. The stents 36 are configured to support the tubular body 34 and seal it against the wall of the false lumen once implanted. Further, as shown, the tubular body 34 is cylindrical in that it has a substantially constant diameter. However, this is not necessary in every case. Each of the stents 36 is a Z-stent. In other words, each of the stents 36 has a substantially annular configuration comprising alternating proximal apices and distal apices, with each proximal apex being joined to each of its adjacent distal apices by a respective strut.

The stents 36 may be formed of any suitable material including spring steel, nitinol, and other known materials. However, nitinol and/or spring steel are preferred. The stents 36 may be self-expanding stents, balloon-expandable stents or stents that use other expansion mechanisms can be used. The stents 36 may be attached to an external surface of the tubular body 34. Alternatively, one or more or all of the stents 36 can be attached to an internal surface of the tubular body 34. The stents 36 can be attached to the tubular body 34 in any manner such as by conventional suturing. The stents may be ring stents.

The stent graft 32 is configured in the expanded condition to have a length 38, and to be hollow along a majority of the length 38. For example, it is hollow along at least 95% of the length 38 in the expanded condition.

The stent graft 32 includes at least one occlusive barrier, for example at least one occlusive gapless graft material barrier 40, across the stent graft 32 to occlude blood flow through an interior of the stent graft 32, in particular to occlude blood flow through the tubular body 34. As shown, stent graft 32 includes a single occlusive gapless graft material barrier 40 across the stent graft, at a proximal end of the stent graft. By gapless, what is meant is that the occlusive graft material barrier 40 contains no holes or openings so that it is completely impervious to blood. It is completely closed so there is no flow through the graft. The stent graft 32 is hollow along an entirety of its length in the expanded condition save for the at least one occlusive barrier 40. The entire transverse cross-section of the stent-graft 32 is occluded by the barrier 40 such that blood cannot flow into or out of the proximal end of the stent graft 32.

In one example, the barrier 40 is continuous with and part of the graft material that forms the tubular body 34. However, in other embodiments, the barrier can be a separate sheet of graft material that is attached to the tubular body such as by suturing. In such embodiments, the barrier is preferably attached to the tubular body so as to be sealed thereto to prevent blood leakage, and the barrier 40 and tubular body 34 can be formed from the same or different graft materials.

As shown in FIG. 5, the barrier 40 does not need to be completely perpendicular to a longitudinal axis of the occluder 30, but is sealed or otherwise connected to the tubular body around the entire circumference of the proximal end of the tubular body 34 so that the barrier 40 occludes blood flow. As shown, the occluder 30 has a diameter 42 greater than 15 mm. In particular, the diameter 42 is greater than 20 mm. In particular, the diameter 42 is greater than 30 mm. These dimensions are particularly suitable for closing a false lumen of dissection where the lumen can be quite large. The diameter 42 may be up to 50 mm.

Figure 6:
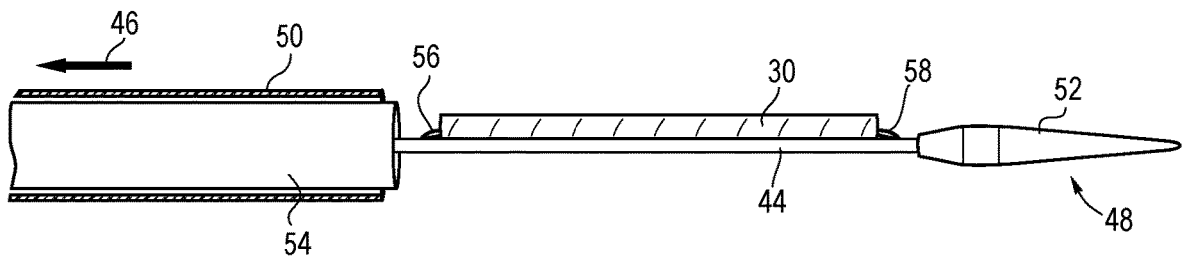
FIG. 6 is a side view of a distal end of a false lumen closure assembly according to an embodiment of the invention, including the false lumen occluder of the embodiment of FIG. 5.
Figure 7:
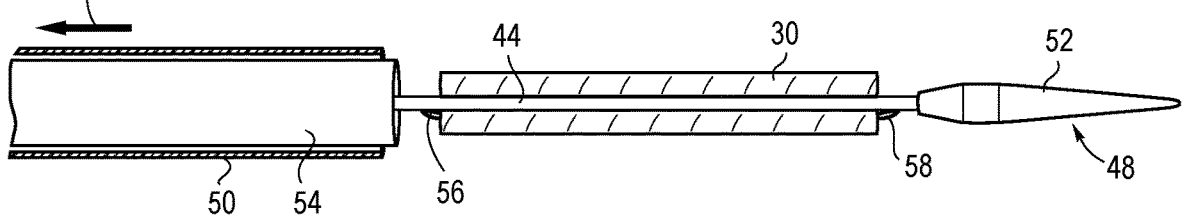
FIG. 7 is another side view of the distal end of the false lumen closure assembly of FIG. 6.

FIGS. 6 and 7 show a distal end of a false lumen closure assembly according to an embodiment of the invention, including the occluder 30 of FIG. 5, but with the occluder 30 in a compressed condition. FIG. 6 is a side view of the distal end of the assembly. FIG. 7 is another side view of the distal end of the assembly, from a direction 90° with respect to the direction of the view of FIG. 6. The false lumen closure assembly is for closing a false lumen in a body vessel using the occluder 30.

As shown, the assembly includes a carrier catheter 44 carrying the false lumen occluder 30. The carrier catheter 44 extends from a proximal end 46 proximal of the false lumen occluder 30 to a distal end 48 distal of the false lumen occluder, and passes the false lumen occluder 30 exteriorly of the stent graft 32. The carrier catheter 44 includes a lumen 45 allowing the carrier catheter 44 to be guided to a target location over a guidewire.

Figure 8:
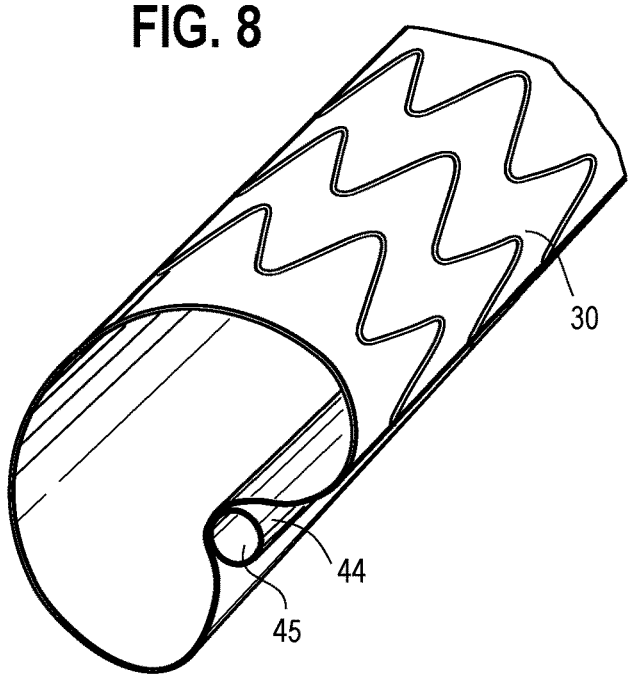
FIG. 8 is a perspective view of part of the false lumen closure assembly of FIGS. 6 and 7.

For further detail, reference is made to FIG. 8 which is a perspective view showing the false lumen occluder 30 on the carrier catheter 44. As can be seen in FIG. 8, the carrier catheter 44 is exterior to the stent graft of the occluder 30. The carrier catheter does not pass through the interior of the occluder 30. In this embodiment, this is achieved by the false lumen occluder 30 including the stent graft 32 thereof being wrapped around the carrier catheter 44. The carrier catheter 44 may sit off-center with respect to the compressed occluder 30.

As shown in FIG. 8, part of the circumference of the compressed stent graft 32 of the occluder 30 is folded radially inwardly to create a passage through which the carrier catheter 44 passes without passing through the occlusive barrier 40.

An advantage of this arrangement is that it allows the occlusive barrier 40 of the occluder 30 to be completely gapless without any apertures or openings since the carrier catheter does not need to pass through it for deployment. This can result in a rapid and effective occlusion once the occluder 30 is deployed.

As also shown, the assembly includes a retractable sheath 50. The compressed false lumen occluder 30 and at least part of the carrier catheter 44 are disposed in a lumen of the retractable sheath 50 to be held within the sheath 50 for delivery. It is noted that for clarity in FIGS. 6 and 7, the section of the sheath 50 around the occluder 30 has been omitted.

As shown, the distal end of the false lumen occluder 30 is restrained by a trigger wire 56 in a conventional manner. It is to be borne in mind that the distal end of the carrier catheter 44 faces proximally with respect to the assembly as a whole. The trigger wire 56 passes from the distal end of the false lumen occluder 30 to an external manipulation section (not shown) of the assembly where it can be controlled and manipulated in a conventional fashion.

As shown, the proximal end of the false lumen occluder 30 is restrained by a trigger wire 58 in a conventional manner. The trigger wire 58 passes from the proximal end of the false lumen occluder 30 to the external manipulation section of the assembly where it can be controlled and manipulated in a conventional fashion. However, one or both trigger wires can be omitted.

As shown, the assembly includes a nose cone dilator 52 at a distal end 48 of the carrier catheter 44. It is noted that the distal end 48 of the carrier catheter 44 is at a distal end of the nose cone dilator 52 so that the distal end of the lumen of the carrier catheter is open to ensure that a guidewire can pass through the lumen 45 of the carrier catheter 44 and out of the distal end of the nose cone 52. The nose cone dilator may include or consist of a balloon, allowing it to be deflated to reduce its profile and make retrieval easier.

The carrier catheter 44 passes from its proximal end 46, which may be at the external manipulation section, through the lumen of the retractable sheath 50, where it passes exteriorly to the occluder 30, and on to the distal end 48 of the carrier catheter 44 at the nose cone dilator 52.

The assembly also includes a pusher member 54 at least partly within the retractable sheath 50 and proximal of the compressed false lumen occluder 30, to limit proximal movement of the false lumen occluder during delivery. That is to say that the distal end of the pusher member 54 is proximal of the compressed false lumen occluder 30 to limit proximal movement of the false lumen occluder 30 during delivery. In this embodiment the pusher member 54 extends from just proximal of the compressed false lumen occluder 30 to the external manipulation section (not shown).

Here, the carrier catheter 44, the pusher member 54, and the retractable sheath are all concentric, although they do not need to be concentric in every embodiment. In any event, the occluder 30 is not concentric with those elements since it is wrapped around the carrier catheter 44.

The pusher member 54 includes a lumen through which the carrier catheter 44 passes. At least at the distal end of the pusher member 54, the pusher member 54 surrounds the carrier catheter 44 and has a greater diameter than the carrier catheter so as to limit movement of the occluder 30 which is carried on the carrier catheter 44 distal of the pusher member 54. In this embodiment, the carrier catheter 44 has a diameter of at least 0.5 mm, in particular a diameter of at least 1 mm.

In this Figure, the false lumen closure assembly for closing a false lumen in a body vessel is assembled as follows. The false lumen occluder 30 described above is wrapped around the carrier catheter 44. In this embodiment, this is performed by compressing the false lumen occluder 30 to the compressed condition, folding a part of the compressed circumference of the stent graft 32 of the occluder 30 radially inwardly to pass around the carrier catheter and placing the occluder 30 on the carrier catheter 44 so that the carrier catheter 44 passes through the passage created by the inward fold. Of course, the folding inwardly of a part of the circumference of the stent graft and the placing of the occluder on the carrier catheter are not necessarily separate or distinct steps but can be performed as part of the same action. The trigger wires 56, 58 are attached and the retractable sheath 50 is placed over the compressed occluder 30. The other parts of the assembly can be assembled in a conventional way at any appropriate point before, after, or during the steps above.

In this embodiment, a method of closing a false lumen in a body vessel using the assembly described above is performed as follows. The distal end of the assembly is guided to a target location in a body vessel as follows. Here, the target location is a false lumen of dissection. In particular, the false lumen is a false lumen caused by an aortic dissection, such as a type B or a residual type A aortic dissection, but other false lumens can be treated in other embodiments. Firstly, a guidewire is guided to the target location using conventional techniques. The assembly is then guided to the target location over the guidewire. In particular, with the guidewire passing through the lumen 45 of the carrier catheter 44, the assembly is advanced along the guidewire until the compressed false lumen occluder 30 is at the target location.

The carrier catheter 44, pusher member 54, and retractable sheath 50 are advanced over the guidewire together to ensure that the occluder 30 is delivered to the target location in its compressed condition. In particular, the pusher member 54 limits proximal movement of the false lumen occluder 30 during delivery, ensuring that it remains in the correct position on the carrier catheter. Furthermore, the retractable sheath 50 retains the occluder 30 in the compressed condition and prevents it from expanding prematurely.

Figure 9:
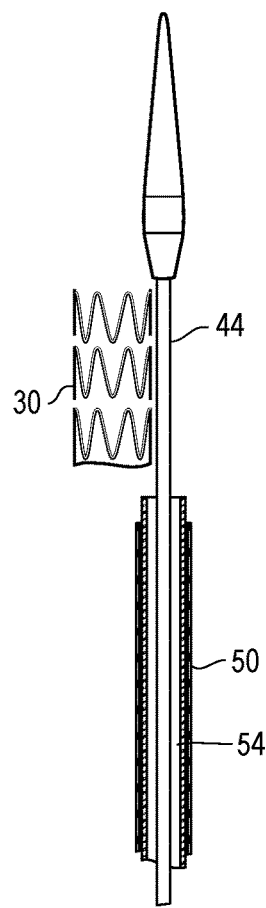
FIGS. 9 and 10 show side views of the distal end of the false lumen closure assembly of FIGS. 6 and 7 after expansion of the occluder.
Figure 10:
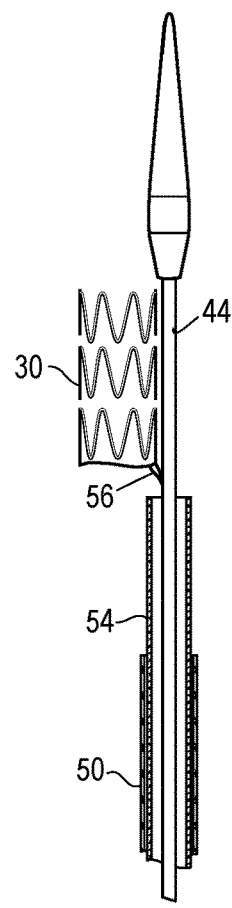

The false lumen occluder 30 is thereby delivered to the false lumen in the body vessel in an over the wire technique. The false lumen occluder 30 is then deployed in the false lumen. The false lumen occluder 30 is deployed in the false lumen by retracting the retractable sheath 50 from the false lumen occluder 30 and then releasing the trigger wires 56, 58 to allow the false lumen occluder to expand in the false lumen. FIGS. 9 and 10 are side views of the distal end of the assembly after expansion of the occluder 30. Using trigger wires provides control during deployment; the graft will not jump. This is advantageous since the graft in some embodiments may be up to 50 mm and deployed from a sheath that is only 22Fr. However, the sheath 50 is not completely removed at this point; it is pulled back to the position of the handle, although the precise point to which it is pulled back can be varied so long as the occluder can expand. The self-expanding stents 36 are then able to expand. Part of the circumference of the stent graft of the occluder 30 is still obstructed by the carrier catheter 44. However, the carrier catheter 44 can be retracted to allow the stents 36 to fully expand to seal the tubular body 34 of the occluder 30 against the false lumen wall. In particular, the dilator tip 52 of the delivery system is retracted between the false lumen occluder 30 and the vessel-wall. The sheath 50 can be used to keep the false lumen occluder 30 at its intended position; if it looks like the occluder 30 is migrating in the distal direction while pulling out the tip 52, the sheath 50 can be moved to the edge of the occluder 30 to keep the occluder 30 in position. Once the tip 52 has been successfully retracted and the occluder 30 successfully implanted, the carrier catheter 44, sheath 50 and pusher catheter 54 can be completely withdrawn. Of course, in other embodiments, a balloon catheter or other mechanism can be used to expand the stents 36.

As can be understood from the above, deploying the false lumen includes enabling the stent graft to expand to seal against the wall of the false lumen such that the at least one occlusive barrier extends across and occludes the false lumen. In particular, the expansion of the stents 36 and sealing of the tubular body 34 against the false lumen wall means that the occlusive barrier 40 extends across the entire lumen available to blood flow and effects an effective occlusion to prevent back flow through the aortic dissection. Furthermore, the fact that the barrier 40 is a gapless graft material barrier means that occlusion can be extremely rapid and effective, since there are no temporary or permanent apertures in the barrier. The occluder 30 can provide instant closure of the false lumen without risk of blood back flow into the false lumen.

As the skilled person will understand from this disclosure, embodiments of the invention are easy to deploy. They are also easy to manufacture as no valve is needed. There is no risk of getting the nosecone trapped in the sleeve of the valve. There is also no risk the distal sleeve can interact with false-lumen-originating ostia of renal arteries for example.

In other examples, instead of the stent graft of the false lumen occluder being wrapped around the carrier catheter, the carrier catheter laterally passes to one side of the compressed false lumen occluder. In such embodiments, in the compressed condition, the false lumen occluder is compressed and positioned entirely to one side of the carrier catheter. In such embodiments, the false lumen occluder is compressed and the carrier catheter is made to lie laterally within the sheath such that the occluder and carrier catheter are in laterally distinct regions.

Figure 11:
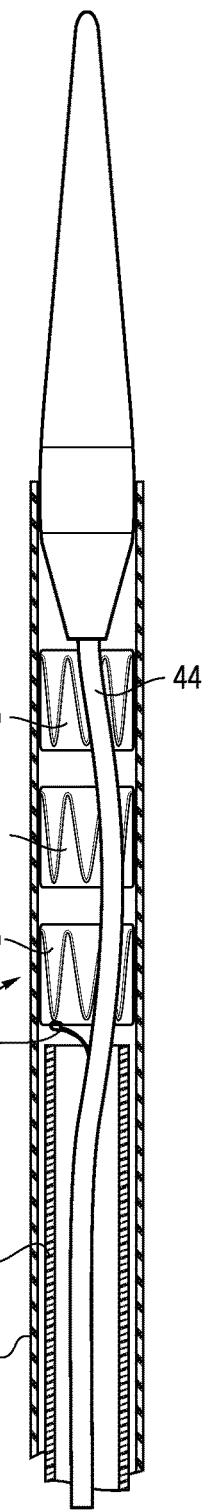
FIG. 11 shows a false lumen closure assembly according to another embodiment of the invention.

The embodiment of FIG. 11 is the same as the embodiment of FIGS. 5 to 10, with the same possible modifications, except that there are three stent segments in the form of three compressed occluders 30 carried by the catheter 44 and held by the retractable sheath 50. Each of the occluders 30 is carried and released in the same way as for the embodiment of FIGS. 5 to 10 except that only the occluder 30 that is carried proximal-most with respect to the assembly (in other words nearest the operator) is restrained by the trigger wire 56 and only the occluder that is carried distal-most with respect to the assembly is restrained by the trigger wire 58.

Although in the embodiments described above the tubular body 34 of the stent graft of the occluder 30 is cylindrical in the expanded condition and has a single obstructive barrier 40, this is not necessary in every embodiment. The stent graft can include any number of obstructive barriers, similar to the obstructive barrier 40 described above, and positioned at any longitudinal position along the stent graft of the occluder 30. Furthermore, the tubular body of the stent graft of the occluder 30 does not need to be cylindrical in the expanded condition.

FIGS. 12-15 show different embodiments of a false lumen occluder for use in the same manner as described above for the false lumen occluder 30. The false lumen occluders of the embodiments of FIGS. 12-15 are the same as the occluder 30 in the above described embodiments, with the same possible modifications, except as described below.

Figure 12:
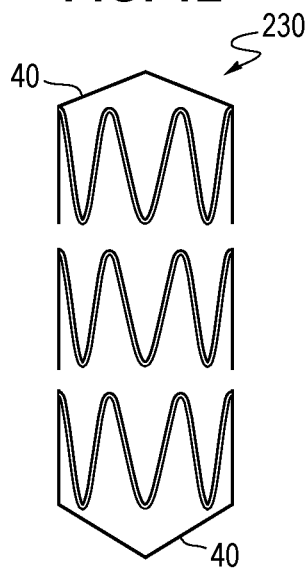
FIGS. 12-15 show false lumen occluders according to different embodiments of the invention.
Figure 13:
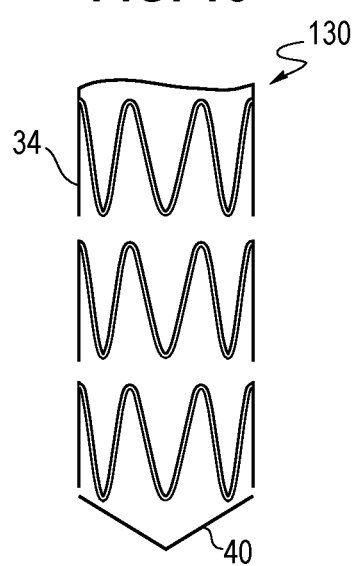
Figure 14:
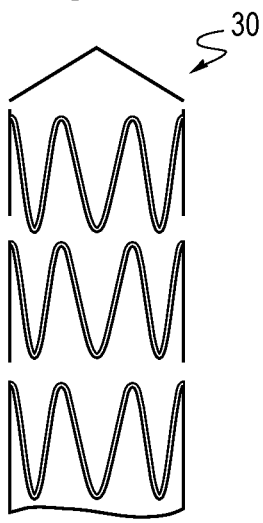

FIGS. 12-15 show the respective occluders in the expanded condition. FIG. 14 shows the false lumen occluder 30 described above. FIG. 13 shows a false lumen occluder 130 which is the same as the false lumen occluder 30 except that the occlusive gapless graft material barrier 40 is at a distal end of the stent graft instead of at the proximal end.

As can be seen in FIG. 13, the barrier 40 does not need to be completely perpendicular to a longitudinal axis of the occluder 130, but is sealed or otherwise connected to the tubular body around the entire circumference of the distal end of the tubular body 34 so that the barrier 40 occludes blood flow.

In the embodiment of FIG. 12, the occluder 230 includes a first barrier 40 at the proximal end of the stent graft as described for the occluder 30 shown in FIG. 14, and a second barrier 40 at the distal end of the stent graft as described for the occluder 130 of FIG. 13.

Figure 15:
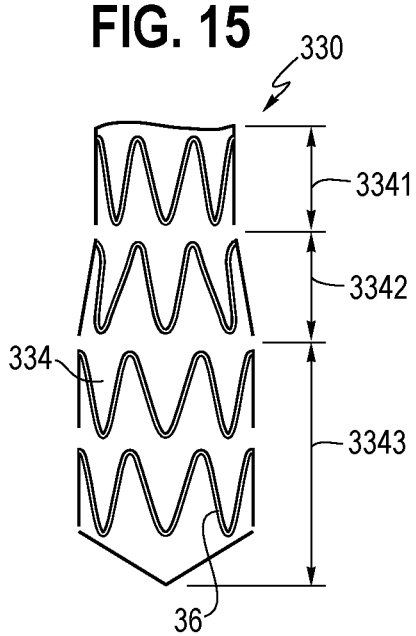

The occluder 330 of the embodiment of FIG. 15 is as per the occluder 130 of the embodiment of FIG. 13. However, for the embodiment of FIG. 15, in the expanded condition, a proximal end of the stent graft has a diameter less than a diameter of the distal end of the stent graft, to facilitate retrieval of the carrier catheter 44, in particular to facilitate retrieval of the tip 52.

In particular, the stent graft includes a taper between the proximal and distal ends thereof to facilitate retrieval of the carrier catheter 44, in particular to facilitate retrieval of the tip 52. The taper causes the reduction in diameter in the expanded condition between the proximal end and the distal end.

In detail, the tubular body 334, which is otherwise as per the tubular body 34 described above, has a proximal cylindrical section 3341, a tapered section 3342, and a distal cylindrical section 3343. In the expanded condition, the proximal section 3341 has a first diameter, the distal section 3343 has a second diameter that is greater than the first diameter, and the tapered section 3342 is between the proximal and distal sections, links the proximal section 3341 to the distal section 3343, and tapers from the second diameter to the first diameter.

Each of the proximal, tapered, and distal sections is supported by at least one of the stents 36 located at that section. In this embodiment, the proximal and tapered sections are each supported by one stent 36 located at the respective section, and the distal section 3343 is supported by two stents 36 located at that section. The number of stents located at each section can be varied.

The stents 36 located at the proximal and tapered sections have a smaller diameter in the expanded condition than the stents located at the distal section, corresponding to the difference in diameter of the respective sections.

Here, it is only the stents located at the distal section 3343 that are configured to seal the stent graft against the false lumen wall. The stents at the proximal and tapered sections are not expected to press against the false lumen wall owing to their lesser diameters; instead, they are configured in the expanded condition to support the shape of the tubular body 334 at that section.

Here, the distal section 3343 is longer than each of the tapered and proximal sections. It preferably has a minimum seal length of 2 stent segments or 35 mm. This is advantageous because it is the wider distal section 3343 that is configured to provide a good seal against the false lumen wall. Furthermore, a short proximal tapered section can also be an advantage if there is thrombus formation already proximal in the false lumen.

Of course, in other embodiments, it is possible to omit the proximal and/or distal sections while still retaining the change in diameter provided by the tapered section. Preferably, the distal section is retained to provide a good seal against the false lumen wall.

Although the occluder 330 of FIG. 15 includes a barrier 40 only at the distal end, barriers can be provided at other locations instead of or in addition to the barrier 40 at the distal end, as described elsewhere in this disclosure.

Figure 16:
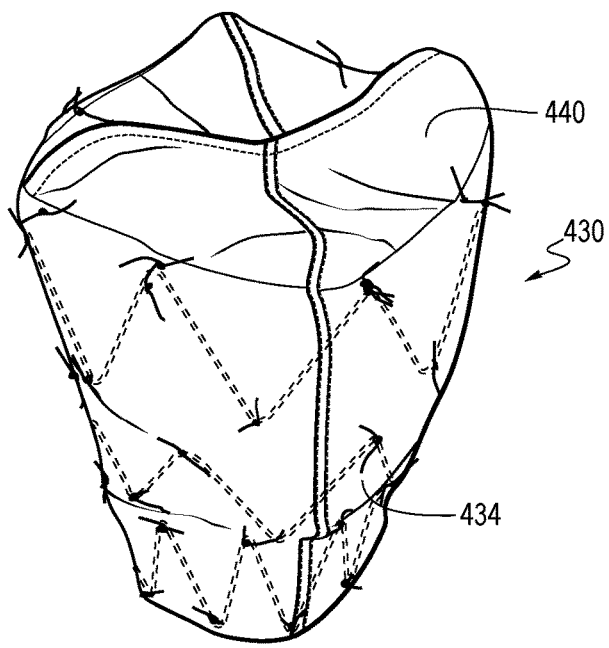
FIGS. 16 and 17 show perspective views of false lumen occluders according to the invention.
Figure 18:
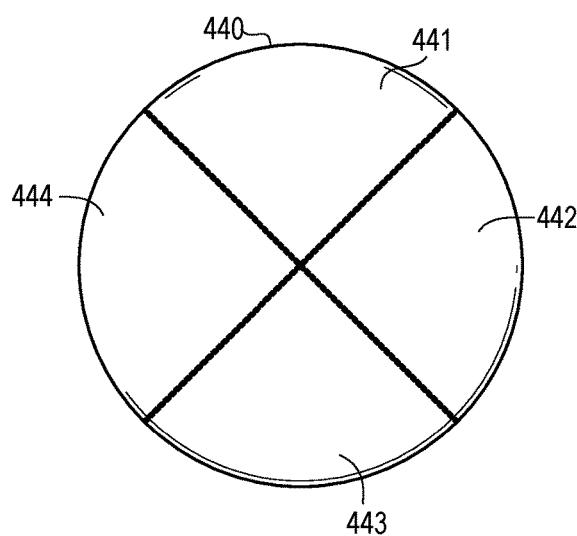
FIG. 18 shows an end view of the embodiment of FIGS. 16 and 17.
Figure 17:
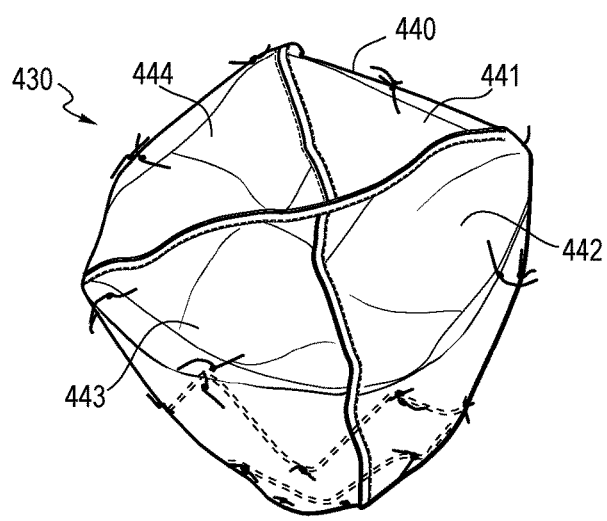

FIGS. 16-17 show an embodiment of a false lumen occluder 430 which is as per the false lumen occluder 30 described above and provides an example of how the barrier is formed. Furthermore, the barriers for any of the embodiments described above can be formed in the manner shown and described for FIGS. 16-17 and its possible modifications.

As shown in FIGS. 16-17, the barrier 440 is continuous with and part of the graft material that forms the tubular body 434 and comprises a plurality of flaps 441, 442, 443, 444.

Here, the barrier comprises a first flap 441, a second flap 442, a third flap 443, and a fourth flap 444. Each of the first, second, third and fourth flaps is a continuous extension of the graft material of about a quarter of the circumference of the tubular body, and is folded across the end of the stent graft such that together the flaps completely cover the otherwise open end of the stent graft. Each flap 441, 442, 443, 444 is attached to its adjacent flaps at its edges, in this example by suturing, so that together the flaps form a gapless graft material barrier 440 across the stent graft.

However, a different number of flaps can be used. However, they are preferably able to be attached so as to form a gapless graft material barrier across the stent graft. Furthermore, the flaps do not need to be continuous with and part of the graft material that forms the material tube in all embodiments; they can in other embodiments be separate from and attached to the tubular body such as by suturing. In such embodiments, the flaps are preferably attached to the tubular body so as to be sealed thereto to prevent blood leakage, and the flaps and tubular body can be formed from the same or different graft materials.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in the abstract accompanying this application are incorporated herein by reference.

The invention claimed is:

1. A false lumen closure assembly for closing a false lumen in a body vessel, including:
a compressed false lumen occluder including a stent graft, the stent graft including at least one occlusive barrier across the stent graft to occlude blood flow through an interior of the stent graft;
a carrier catheter carrying the false lumen occluder, and extending from a proximal end proximal of the false lumen occluder to a distal end distal of the false lumen occluder, and passing the false lumen occluder exteriorly of the stent graft on one side of the stent graft, such that the stent graft is at least partially wrapped around the carrier catheter;
a retractable sheath;
wherein the compressed false lumen occluder and at least part of the carrier catheter are disposed in a lumen of the retractable sheath.

2. The assembly of claim 1, wherein the stent graft has a length and is hollow along a majority of the length in an expanded condition, optionally along at least 95% of the length in an expanded condition.

3. The assembly of claim 1, wherein the carrier catheter is longitudinally offset from a longitudinal axis of the retractable sheath.

4. The assembly of claim 1, further including a pusher member at least partly within the retractable sheath and distal of the compressed false lumen occluder, to limit movement of the false lumen occluder during delivery.

5. The assembly of claim 1, wherein the stent graft has a length and is hollow along an entirety of the length in an expanded condition save for the at least one occlusive barrier.

6. The assembly of claim 1, wherein each of the at least one occlusive barrier is a gapless graft material barrier across the stent graft.

7. The assembly of claim 1, wherein the at least one occlusive barrier includes an occlusive barrier at a distal end of the stent graft.

8. The assembly of claim 1, wherein the at least one occlusive barrier includes an occlusive barrier at a proximal end of the stent graft.

9. The assembly of claim 1, wherein the at least one occlusive barrier comprises an occlusive barrier at the proximal end of the stent graft and an occlusive barrier at the distal end of the stent graft.

10. The assembly of claim 1, wherein the carrier catheter has a diameter of at least 0.5 mm.

11. The assembly of claim 1, wherein the carrier catheter laterally passes the compressed false lumen occluder.

12. The assembly of claim 1, wherein, in an expanded condition, a proximal end of the stent graft has a diameter less than a diameter of the distal end of the stent graft, to facilitate retrieval of the carrier catheter.

13. The assembly of claim 12, wherein the stent graft includes a taper between the proximal and distal ends thereof.

14. A false lumen closure assembly for closing a false lumen in a body vessel, including:
- an elongate carrier catheter having a proximal end, a distal end, an inner lumen configured to extend over a guidewire catheter, and a nose cone dilator at the proximal end of the elongate carrier catheter;
- a compressed false lumen occluder having a proximal end, a distal end and including a stent graft having at least one occlusive barrier across an end of the stent graft to occlude blood flow through an interior of the stent graft; and
- a retractable sheath disposed over the elongate carrier catheter and the compressed false lumen occluder;
- wherein the elongate carrier catheter extends beyond the proximal end of the false lumen occluder to beyond the distal end of the false lumen occluder, and passes the false lumen occluder exteriorly of the stent graft on one side of the stent graft, such that the stent graft is at least partially wrapped around the elongate carrier catheter.

15. The occluder of claim 14, wherein a diameter of the stent graft is greater than 20 mm, optionally greater than 30 mm.

16. The assembly of claim 14, wherein the elongate carrier catheter is longitudinally offset from a longitudinal axis of the retractable sheath.

17. The assembly of claim 14, further including a pusher member at least partly within the retractable sheath and distal of the compressed false lumen occluder, to limit movement of the false lumen occluder during delivery.

18. The assembly of claim 1, wherein an end of the false lumen occluder is releasably attached to the carrier catheter.

19. The assembly of claim 15, wherein an end of the false lumen occluder is releasably attached to the elongate carrier catheter.

20. A false lumen closure assembly for closing a false lumen in a body vessel, including:
- a compressed false lumen plug including a stent graft, the stent graft including at least one occlusive barrier across the stent graft to occlude blood flow through an interior of the stent graft;
- a carrier catheter carrying the false lumen plug, the carrier catheter extending from a proximal end proximal of the false lumen plug to a distal end distal of the false lumen plug, and passing the false lumen plug exteriorly of the stent graft;
- a retractable sheath;
- wherein the carrier catheter and compressed false lumen plug are disposed in a lumen of the retractable sheath.

* * * * *